(12) United States Patent
Reynard

(10) Patent No.: US 12,042,432 B1
(45) Date of Patent: Jul. 23, 2024

(54) METHOD AND DEVICE FOR THE TREATMENT OF GLAUCOMA

(71) Applicant: Michael Reynard, Santa Monica, CA (US)

(72) Inventor: Michael Reynard, Santa Monica, CA (US)

( * ) Notice: Subject to any disclaimer, the term of this patent is extended or adjusted under 35 U.S.C. 154(b) by 0 days.

(21) Appl. No.: 18/410,218

(22) Filed: Jan. 11, 2024

(51) Int. Cl.
| | | |
|---|---|---|
| *A61F 9/007* | (2006.01) | |
| *A61N 1/05* | (2006.01) | |
| *A61N 1/36* | (2006.01) | |
| *A61N 1/378* | (2006.01) | |
| *A61M 27/00* | (2006.01) | |

(52) U.S. Cl.
CPC ........ *A61F 9/00781* (2013.01); *A61N 1/0526* (2013.01); *A61N 1/36046* (2013.01); *A61N 1/378* (2013.01); *A61M 27/002* (2013.01); *A61M 2210/0612* (2013.01)

(58) Field of Classification Search
CPC ............ A61F 2009/00891; A61F 9/007; A61F 9/00781; A61B 3/16; A61B 2562/0247; A61M 27/002; A61M 2027/004; A61M 2210/0612
See application file for complete search history.

(56) References Cited

U.S. PATENT DOCUMENTS

| | | |
|---|---|---|
| 3,398,069 A | 8/1968 | Juda |
| 3,399,131 A | 8/1968 | Edouard et al. |
| 3,441,488 A | 4/1969 | Onstott |
| 4,105,528 A | 8/1978 | Hasebe |
| 4,495,048 A | 1/1985 | Murakami et al. |
| 4,603,697 A | 8/1986 | Kamerling |
| 4,758,322 A | 7/1988 | Sioli |
| 4,969,986 A | 11/1990 | McIntyre et al. |
| 5,005,577 A | 4/1991 | Frenkel |
| 5,024,223 A | 6/1991 | Chow |
| 5,071,408 A | 12/1991 | Ahmed |

(Continued)

FOREIGN PATENT DOCUMENTS

WO    1999/016934 A1    4/1999

OTHER PUBLICATIONS

Cara Young and Leonard Seibold, "24-Hour IOOP Monitoring: Current State and Future Directions", Glaucoma Physician, Mar. 2018.

(Continued)

*Primary Examiner* — Phillip A Gray
*Assistant Examiner* — Anna E Goldberg-Richmeier
(74) *Attorney, Agent, or Firm* — Richard A. Baker, Jr.

(57) ABSTRACT

An ocular electrolysis device is described that may include a diverting tube configured for insertion into an eye. The ocular electrolysis device may include an electrolysis chamber mechanically attached to the diverting tube such that aqueous from the eye enters the electrolysis chamber through the diverting tube. The ocular electrolysis device may include a pressure sensor located in the electrolysis chamber. The ocular electrolysis device may include a pair of electrodes located in the electrolysis chamber. The ocular electrolysis device may include a controller electrically connected to the pair of the electrodes and the pressure sensor, where the controller regulates electrolysis of the aqueous in the electrolysis chamber based on input from the pressure sensor through power levels at the pair of the electrodes.

20 Claims, 8 Drawing Sheets

(56) References Cited

U.S. PATENT DOCUMENTS

| | | | |
|---|---|---|---|
| 5,076,902 | A | 12/1991 | Joshima et al. |
| 5,112,463 | A | 5/1992 | Zhang et al. |
| D330,766 | S | 11/1992 | Mann |
| 5,178,604 | A | 1/1993 | Baerveldt et al. |
| 5,194,132 | A | 3/1993 | Hartman et al. |
| 5,288,383 | A | 2/1994 | Sparwald et al. |
| 5,558,629 | A | 9/1996 | Baerveldt et al. |
| 5,725,493 | A | 3/1998 | Avery et al. |
| 5,843,297 | A | 12/1998 | Schmid et al. |
| 5,935,155 | A | 8/1999 | Humayun et al. |
| 6,071,386 | A | 6/2000 | Puthawala |
| 6,533,768 | B1 | 3/2003 | Hill |
| RE38,066 | E | 4/2003 | Puthawala |
| 6,638,413 | B1 | 10/2003 | Weinberg et al. |
| 6,712,764 | B2 | 3/2004 | Jeffries et al. |
| 6,716,331 | B2 | 4/2004 | Chikuma |
| 6,749,568 | B2 | 6/2004 | Fleischman et al. |
| 6,800,206 | B2 | 10/2004 | Robinson |
| 7,452,449 | B2 | 11/2008 | Weinberg et al. |
| 7,638,021 | B2 | 12/2009 | Blenkiron et al. |
| 7,720,549 | B2 | 5/2010 | Schroeppel et al. |
| 7,828,942 | B2 | 11/2010 | Cocking |
| 7,909,968 | B2 | 3/2011 | Hallenbeck |
| 8,048,276 | B2 | 11/2011 | Balestrino et al. |
| 8,062,500 | B2 | 11/2011 | Sumita |
| 8,075,749 | B2 | 12/2011 | Mcalister |
| 8,123,916 | B2 | 2/2012 | Blenkiron et al. |
| 8,131,375 | B2 | 3/2012 | Greenberg et al. |
| 8,195,266 | B2 | 6/2012 | Whalen et al. |
| 8,353,906 | B2 | 1/2013 | Joshi et al. |
| 8,380,326 | B2 | 2/2013 | Greenberg et al. |
| 8,419,673 | B2 | 4/2013 | Rickard |
| 8,428,728 | B2 | 4/2013 | Sachs |
| 8,506,515 | B2 | 8/2013 | Burns et al. |
| 8,518,680 | B2 | 8/2013 | Kuhry et al. |
| 8,527,055 | B2 | 9/2013 | Rickard |
| 8,606,358 | B2 | 12/2013 | Sachs |
| 8,608,664 | B2 | 12/2013 | Kunitake et al. |
| 8,691,060 | B2 | 4/2014 | Haryu et al. |
| 8,709,220 | B2 | 4/2014 | Nakazawa et al. |
| 8,894,829 | B2 | 11/2014 | Haryu et al. |
| 8,918,181 | B2 | 12/2014 | Ackermann et al. |
| 8,939,906 | B2 | 1/2015 | Huang et al. |
| 8,961,750 | B2 | 2/2015 | Zadorozhny et al. |
| 8,964,646 | B2 | 2/2015 | Ohayon et al. |
| 9,011,651 | B2 | 4/2015 | Greenbaum |
| 9,066,782 | B2 | 6/2015 | Niksch et al. |
| 9,095,723 | B2 | 8/2015 | Ackermann et al. |
| 9,125,290 | B2 | 9/2015 | Greenberg et al. |
| 9,226,850 | B2 | 1/2016 | Baerveldt et al. |
| 9,254,168 | B2 | 2/2016 | Palanker |
| 9,268,153 | B2 | 2/2016 | Blum et al. |
| 9,271,869 | B2 | 3/2016 | Horvath et al. |
| 9,307,905 | B2 | 4/2016 | Shen et al. |
| 9,333,115 | B2 | 5/2016 | Dos Santos |
| 9,339,187 | B2 | 5/2016 | Rickard |
| 9,375,348 | B2 | 6/2016 | Gunn |
| 9,409,011 | B2 | 8/2016 | Tai et al. |
| 9,504,606 | B2 | 11/2016 | Gunn et al. |
| 9,700,721 | B2 | 7/2017 | Anthony, V et al. |
| 10,252,048 | B2 | 4/2019 | Loudin et al. |
| 10,335,030 | B2 | 7/2019 | Alhourani |
| 10,391,312 | B2 | 8/2019 | Masko et al. |
| 10,426,958 | B2 | 10/2019 | Loudin et al. |
| 10,492,948 | B2 | 12/2019 | Baerveldt |
| 10,548,769 | B2 | 2/2020 | Venkatraman et al. |
| 10,610,686 | B2 | 4/2020 | Lee |
| 10,682,514 | B2 | 6/2020 | Mowery et al. |
| 10,835,748 | B2 | 11/2020 | Ackermann et al. |
| 10,987,033 | B2 | 4/2021 | Martin et al. |
| 11,191,961 | B2 | 12/2021 | Simon et al. |
| 11,480,813 | B2 | 10/2022 | Kubota et al. |
| 2004/0186533 | A1 | 9/2004 | Greenberg et al. |
| 2007/0173905 | A1 | 7/2007 | Greenberg et al. |
| 2011/0022118 | A1 | 1/2011 | Rickard |
| 2011/0132751 | A1 | 6/2011 | Smedley |
| 2012/0130398 | A1 | 5/2012 | Ackermann et al. |
| 2012/0140167 | A1 | 6/2012 | Blum |
| 2015/0088156 | A1 | 3/2015 | Ackermann et al. |
| 2015/0211131 | A1 | 7/2015 | Jacobs |
| 2015/0230984 | A1* | 8/2015 | Gunn ............... F04B 19/006 604/9 |
| 2015/0335900 | A1 | 11/2015 | Ackermann et al. |
| 2016/0015265 | A1 | 1/2016 | Mandel et al. |
| 2017/0007834 | A1 | 1/2017 | Irazoqui et al. |
| 2017/0127941 | A1 | 5/2017 | Ostermeier et al. |
| 2017/0258635 | A1 | 9/2017 | Reynard |
| 2018/0325733 | A1* | 11/2018 | Camras ............... A61F 9/00781 |
| 2020/0179705 | A1 | 6/2020 | Ternes et al. |
| 2020/0185951 | A1 | 6/2020 | Osada |
| 2020/0188660 | A1 | 6/2020 | Franke et al. |
| 2020/0330765 | A1* | 10/2020 | Reynard ............... A61N 1/3603 |
| 2020/0368064 | A1 | 11/2020 | Irazoqui et al. |
| 2022/0395634 | A1* | 12/2022 | Mcdermott ............ G16H 20/17 |
| 2023/0119048 | A1 | 4/2023 | Irazoqui et al. |
| 2023/0181312 | A1 | 6/2023 | Wortz et al. |

OTHER PUBLICATIONS

"Ahmed Glaucoma Valve", ad from New World Medical, Inc, EyeNet Magazine, unknown date.
"Ahmed Glaucoma Valve", ad from New World Medical, Inc, purportedly from Ophthalmology Times, Feb. 15, 1999.
Rodney Grimes, "Medical Device Design", applianceDESIGN, Jun. 2017.
"Analytical Toolkit for the Optimization of Battery Electrode Materials", Malvern Panalytical, 2020.
Carl Falcon, "Improving Data Transfer and Battery Life for Implanted Devices", Medical Device and Diagnostic Industry, Jun. 2005.
John Rogers, "Electronics for the Human Body", JAMA (vol. 313:6), Feb. 10, 2015.
Enrique Spinelli and Marcelo Haberman, "Insulating electrodes: a review on biopotential front ends for dielectric skin-electrode interfaces", Physiol. Meas. 31 S183, Sep. 10, 2010 (Abstract only).
H Burkhard Dick, Ronald D Gerste, "Future Intraocular Lens Technologies", Ophthalomology, Dec. 2020 (Abstract only).
"Innovation in Glaucoma", Glaucoma Today, Winter 2010.
Sorachon Yoriya, "Effect of Inter-Electrode Spacing on Electrolyte Properties and Morphologies of Anodic $TiO_2$ Nanotube Array Films", Int. J. Electrochem. Sci., Oct. 1, 2012.
Desiree Ifft, "Keeping a Closer Watch on IOP", Glaucoma Physician, Dec. 2017.
Jeremy Lug and Randolph Sablich, "Just Make it Smaller", MDTmag.com, Jul./Aug. 2012.
Jorge Alvarado, "Predicting and Improving the Outcomes of SLT Therapy", Special section sponsored by Lumenis, undated.
Prethy Rao, Edward Wood, and Tamer Mahmoud, "Current Status of Subretinal Delivery Devices", Retinal Physician, Apr. 2023.
David Schatz, "Wireless Power for Medical Devices", Medical Device and Diagnostic Industry, Jul. 2013.
"Electrolysis of Water", US Department of Energy, Energy Education and Workforce Development, undated.
"Electrolysis of Water", Wikipedia, Mar. 13, 2016.
"Electrolysis: Splitting water", undated.
Mark Brinton, Jae Lim Chung, Andrea Kossler, Koung Hoon Kook, Jim Loudin, Manfred Franke, and Daniel Palanker, "Electronic enhancement of tear secretion", J Neural Eng, Feb. 2016.
Megan Brooks, "FDA Clears New Contact Lens that Senses Eye Pressure Changes", Medscape Medical News, Mar. 7, 2016.
Shiyi Liu, Xueling Meng, Jianwei Zhang, Junseok Chae, "A wireless fully-passive acquisition of biopotentials", Biosensors and Bioelectronics, Aug. 15, 2019.
Mesut Sahin and Victor Pikov, "Wireless Microstimulators for Neural Prosthetics", Crit Rev Biomed Eng., Jul. 2011.
Shiyi Liu, Ali Navaei, Xueling Meng, Mehdi Nikkhah, Junseok Chae, "Wireless Passive Stimulation of Engineered Cardiac Tissues", ACS Sens., 2017.

(56) References Cited

OTHER PUBLICATIONS

Orzalesi, N. et al. "Effect of Timolol, Latanaprost, and Dorzolamide on Circadian IOP in Glaucoma or Ocular Hypertension", Invest Ophthalmol Vis Sci, vol. 9, Aug. 2000, pp. 2566-2573.
Nagai, N. et al. "Existence of optimum space between electrodes on hydrogen production by water electrolysis", Int J Hyd Energy, vol. 28, 2003, pp. 35-41.
Andrew Rabinowitz, "A New Look at Glaucoma Shunts", Ophthalmology Management, Apr. 2009.
Manik Goel, Renata G. Picciani, Richard K. Lee and Sanjoy K. Bhattacharya, "Aqueous Humor Dynamics: a Review", The Open Ophthalmology Journal, 2010, 4, 52-59.
Parthopratim Dutta Majumder, "Anatomy of Anterior Chamber", webpage downloaded on Apr. 6, 2021 rfom www.eophtha.com/posts/anatomy-of-anterior-chamber#:~:text=Anterior chamber is an angular, a part of cilliary body. &text=Anterior chamber is 3 mm,ml of the aqueous humour.
Lance Lyons and Arthur Sit, "An Update on Implantable IOP Monitoring", Glaucoma Physician, Mar. 2021.
Anna DO and Joseph Panarelli, "Changes in Glaucoma Management Following Diurnal Home Tonometry", Glaucoma Physician, Mar. 2023.
"Electoloysis of Salt Water", Aquarius Education & Public Outreach, undated.
Thierry Malvache, "Microcables Open up New Dimensions in Invasive Surgery", MDTmag.com, Aug. 2018.
Susan Zaks, "Sensors Address Critical Healthcare Needs", MDTmag.com, Aug. 2018.
"The Ahmed Glaucoma Valve", New World Medical, Feb. 2018.

\* cited by examiner

801 — Implantation of an electrolysis device on the surface of the eye with a diversion tube that extends into the anterior chamber of an eye

802 — Pressure transmitted by the aqueous is measured by a pressure sensor within the electrolysis chamber in the electrolysis device

803 — A programmed electronic controller is activated to apply electrical current to paired electrodes in the electrolysis chamber. The duration and delivery of electrical current to the electrodes is regulated by the controller with feedback from the pressure sensor

804 — Electrolysis of aqueous in the electrolysis chamber results in gas that escapes through a gas permeable roof. Cessation or reduction or electrolysis occurs when the pressure reaches a programmed threshold

805 — The electronic controller is programmed to send electronic signals to warn of power issues and to transmit data acquired by the pressure sensor. The controller is also programmed to receive communication that adjusts thresholds for delivery of electrical current to electrodes

FIG. 8

METHOD AND DEVICE FOR THE TREATMENT OF GLAUCOMA

CROSS-REFERENCE

This is a priority patent application. This patent application is related to US Patent Publication 2017/0258635, "Method and device for electrolysis of aqueous humor to treat glaucoma", published for inventor Michael Reynard on Sep. 14, 2017, said patent publication incorporated herein by reference. This patent application is also related to US Patent Publication 2020/0330765, "Method and device for electrolysis of aqueous humor to treat glaucoma", published for inventor Michael Reynard on Oct. 22, 2020, said patent publication incorporated herein by reference.

FIELD OF THE INVENTIONS

The present inventions relate to treatments for glaucoma, and more particularly, to glaucoma devices and methods that reduce the volume of aqueous humor in the anterior chamber of the eye at a controlled rate.

BACKGROUND OF THE INVENTIONS

Glaucoma is a blinding condition that is associated with elevation of intraocular pressure. The intraocular pressure in the eye is maintained by the production and drainage of aqueous humor (aqueous), a clear fluid that mainly occupies the anterior chamber of the eye. The anterior chamber of the eye has a volume of 250 microliters. Aqueous humor normally drains from the anterior chamber through the trabecular meshwork of the eye and into outflow collector channels at a rate of 2 to 3 microliters per minute.

Glaucoma is commonly caused by impaired drainage of aqueous at the level of the trabecular meshwork or outflow collector channel. Elevated intraocular pressure resulting from impaired drainage can result in damage to the optic nerve and permanent loss of vision. Various methods have been used to reduce the production of aqueous humor or improve its drainage by means of medications, surgery, and implants.

The effectiveness of pharmacologic treatment is limited by physiologic variations of intraocular pressure. Diurnal variation is the most notable example of physiologic fluctuation of intraocular pressure. The diurnal variation of intraocular pressure in normal subjects during daytime hours varies between 3-6 mm Hg. In patients with glaucoma, the 24-hour variation of intraocular pressure can be as high as 18 mm Hg. The pressure-lowering effect of medications applied during the day dissipates towards the end of the day and may not be present during nocturnal hours when intraocular pressure may be at its highest level.

Pharmacologic and surgical treatment for glaucoma is expensive and not available to many people who have limited income or who live in remote areas. Medications and invasive surgery for glaucoma have significant risks for complications, including hypotony and infection. Many patients with glaucoma require multiple forms of therapy to control their condition.

The present inventions provide a method and device for changing aqueous humor into gasses that dissipate into the atmosphere. Aqueous humor from the anterior chamber is diverted into a device where the intraocular pressure is measured and electrolysis is applied in a regulated manner to control the level of intraocular pressure on a 24-hour basis.

SUMMARY OF THE INVENTIONS

In some aspects, the techniques described herein relate to an ocular electrolysis device including: a diverting tube configured for insertion into an eye; an electrolysis chamber mechanically attached to the diverting tube such that aqueous from the eye enters the electrolysis chamber through the diverting tube; a pressure sensor located in the electrolysis chamber; a pair of electrodes located in the electrolysis chamber; a power source electrically connected to a controller; and the controller electrically connected to the pair of the electrodes and the pressure sensor, where the controller regulates electrolysis in the electrolysis chamber based on input from the pressure sensor through power levels at the pair of the electrodes.

In some aspects, the techniques described herein relate to an ocular electrolysis device configured for attachment to the eye.

In some aspects, the techniques described herein relate to an ocular electrolysis device further including eyelets for facilitating the attachment to the eye.

In some aspects, the techniques described herein relate to an ocular electrolysis device where the electrolysis chamber has a gas-permeable surface.

In some aspects, the techniques described herein relate to an ocular electrolysis device where the electrolysis chamber has a surface with perforations.

In some aspects, the techniques described herein relate to an ocular electrolysis device further including a voltage regulator electrically connected to the pair of the electrodes and the controller.

In some aspects, the techniques described herein relate to an ocular electrolysis device further including an antenna electrically connected to the controller.

In some aspects, the techniques described herein relate to an ocular electrolysis device wherein the power source includes a solar cell.

In some aspects, the techniques described herein relate to a method for treating glaucoma including: implanting an ocular electrolysis device on a surface of an eye; inserting a diverting tube attached to the ocular electrolysis device into an anterior chamber of the eye, where aqueous from the anterior chamber flows into a electrolysis chamber in the ocular electrolysis device; measuring a pressure measurement in the eye with a pressure sensor located in the electrolysis chamber; reading the pressure measurement with a controller, said controller electrically connected to the pressure sensor; applying current and voltage from a power source under direction of the controller to a pair of electrodes in the electrolysis chamber, causing electrolysis of the aqueous to occur in the electrolysis chamber; and directing, by the controller, the current and the voltage based on the pressure measurement.

In some aspects, the techniques described herein relate to a method for treating the glaucoma where the electrolysis chamber has a gas permeable surface allowing gas to escape the electrolysis chamber.

In some aspects, the techniques described herein relate to a method for treating the glaucoma further including using the pressure measurement by the controller to determine the voltage on the pair of the electrodes.

In some aspects, the techniques described herein relate to a method for treating the glaucoma further including using the pressure measurement by the controller to determine the current on the pair of the electrodes.

In some aspects, the techniques described herein relate to a method for treating the glaucoma further including using the pressure measurement by the controller to determine a frequency of the voltage on the pair of the electrodes.

In some aspects, the techniques described herein relate to a method for treating the glaucoma further including sending, via an antenna, a message with information regarding the ocular electrolysis device.

In some aspects, the techniques described herein relate to a method for treating the glaucoma where the information is the pressure measurement of the aqueous in the electrolysis chamber.

In some aspects, the techniques described herein relate to a method for treating the glaucoma where the information relates to a status of the power source.

In some aspects, the techniques described herein relate to a method for treating the glaucoma further including receiving, via an antenna, a message with a parameter for the ocular electrolysis device.

In some aspects, the techniques described herein relate to a method for treating the glaucoma where the parameter includes a threshold for the pressure measurement of the aqueous in the electrolysis chamber.

In some aspects, the techniques described herein relate to a method for treating the glaucoma where the parameter is a critical low-pressure threshold for the pressure measurement of the aqueous in the electrolysis chamber.

In some aspects, the techniques described herein relate to a method for treating the glaucoma further including turning off the electrodes by the controller when the pressure measurement of the aqueous in the electrolysis chamber is below the critical low-pressure threshold.

In some aspects, the techniques described herein relate to a method for treating the glaucoma where the parameter is a critical high-pressure threshold for the pressure measurement of the aqueous in the electrolysis chamber.

In some aspects, the techniques described herein relate to a method for treating the glaucoma further including turning off the electrodes by the controller when the pressure measurement of the aqueous in the electrolysis chamber is above the critical high-pressure threshold and when the pressure measurement of the aqueous in the electrolysis chamber is increasing.

BRIEF DESCRIPTION OF THE DRAWINGS

FIG. 8 is a block diagram of the operational steps of an ocular electrolysis device.

DETAILED DESCRIPTION OF THE INVENTIONS

All illustrations of the drawings are for the purpose of describing selected versions of the present invention and are not intended to limit the scope of the present invention.

Figure 1:
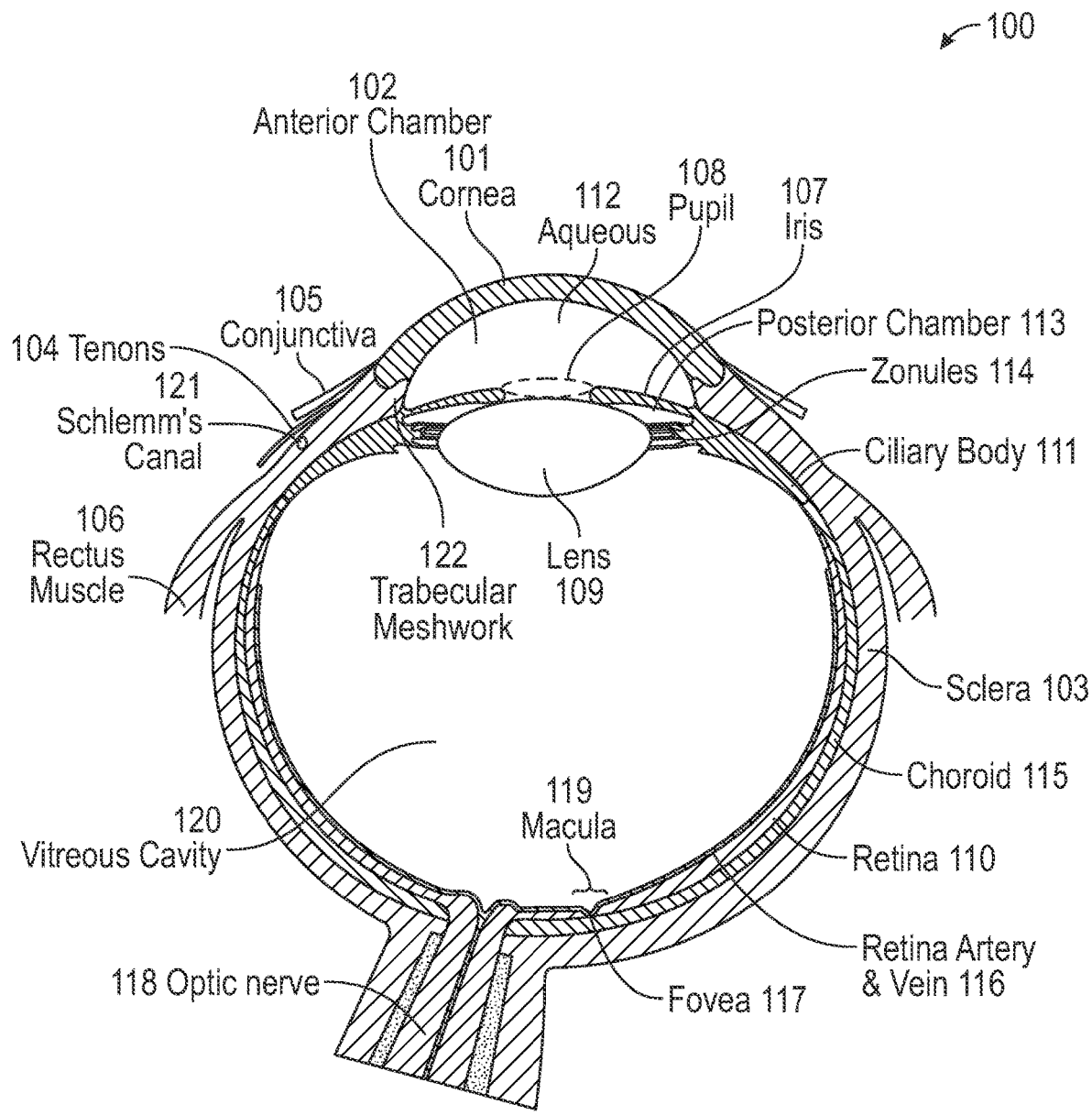
FIG. 1 is a cross-section of a mammalian eye showing the anatomic details.
Figure 2:
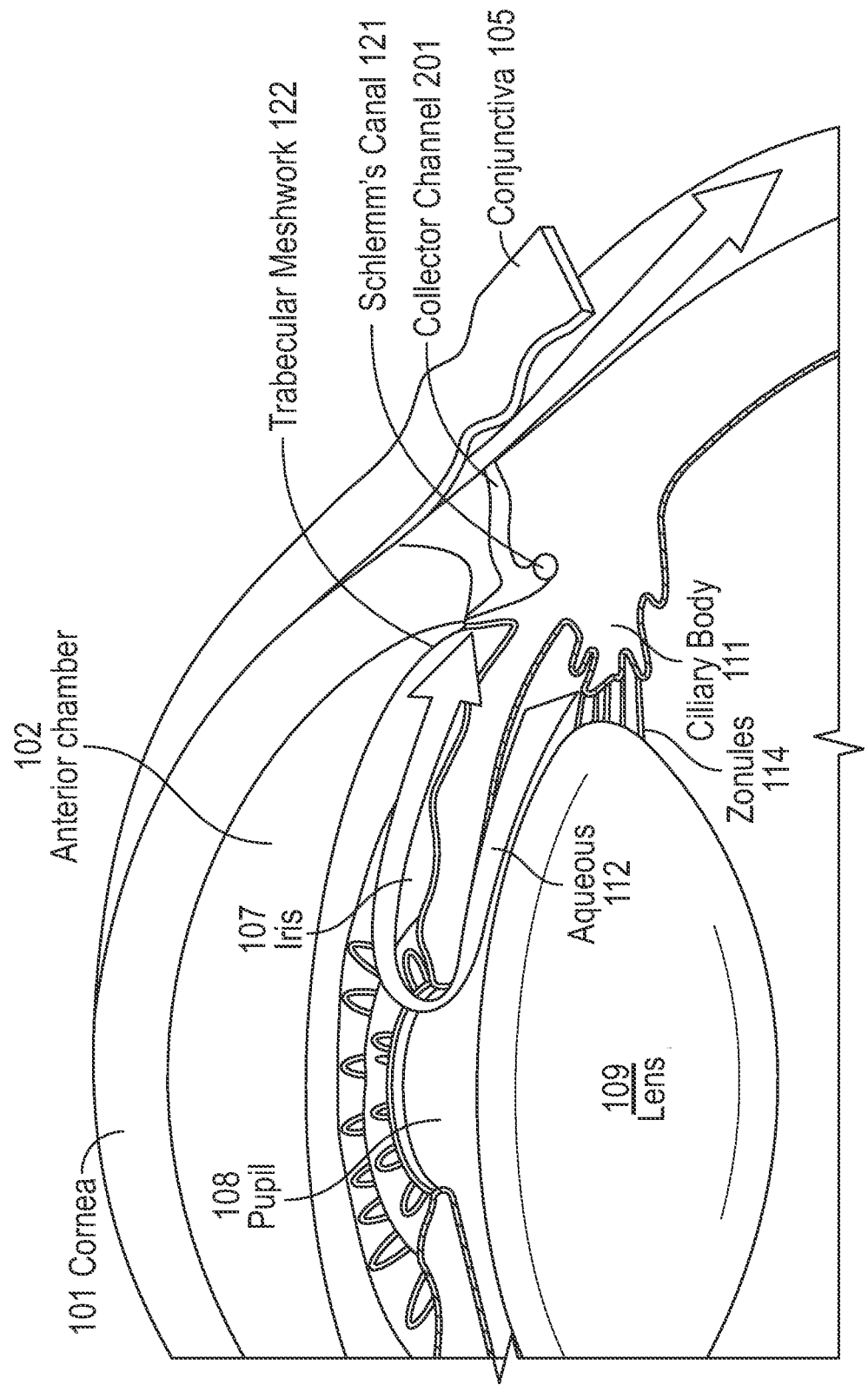
FIG. 2 is a cross-section of a mammalian eye showing fluid of aqueous through the pupil.

FIG. 1 and FIG. 2 illustrate structures of the mammalian eye 100 so as to provide background for relevant anatomical terms and the physiologic basis of the subject invention. It should be apparent that certain anatomic details have been omitted for the sake of clarity and explanation.

In FIG. 1 the cornea 101 forms the anterior portion of the eye 100. The cornea 101 consists of transparent tissue composed of collagen. The cornea 101 demarcates the front boundary of the anterior chamber 102. The remaining outer wall of the eye 100 is the sclera 103. The sclera 103 is covered by Tenon's capsule 104 and conjunctiva 105. The vertical axis and horizontal axis of the eye 100 each have a pair of rectus muscles 106 that serve to move the eye 100 in different directions. The iris 107 is the colored portion of the eye 100 that is visible through the cornea 101. The center of the iris 107 has a round aperture known as the pupil 108. Light travels through the pupil 108 and enters the lens 109 that focuses light on the retina 110 after the light travels through the vitreous cavity 120. The iris 107 forms the posterior boundary of the anterior chamber 102. Behind the iris 107 is the posterior chamber 113. The aqueous 112 is located between the cornea 101 and the lens 109, and in the posterior chamber 113. Between the base of the iris 107 and cornea 101 is the trabecular meshwork 122. The ciliary body 111 is adjacent to the posterior chamber 113 and the zonules 114. The posterior portion of the eye 100 consists of the vitreous cavity 120, a network of arteries and veins 116, a retina 110, a choroid 115, an optic nerve 118, a macula 119, and a fovea 117.

FIG. 2 illustrates that the base of the iris 107 is continuous with the ciliary body 111 which produces aqueous humor (aqueous) 112. The aqueous 112 maintains intraocular pressure and provides nutrients to the cornea 101 and lens 109. The aqueous humor 112 flows between the iris 107 and lens 109, and through the pupil 108. The aqueous humor 112 enters the anterior chamber 102 and drains into a network of tissue known as the trabecular meshwork 122 and passes into Schlemm's canal 121. Schlemm's canal 121 is drained by 25-30 collector channels 201. Intraocular pressure is generally determined by a balance between the resistance to aqueous 112 outflow from the anterior chamber 102 and the production of aqueous 112 from the ciliary body 111.

Figure 3:
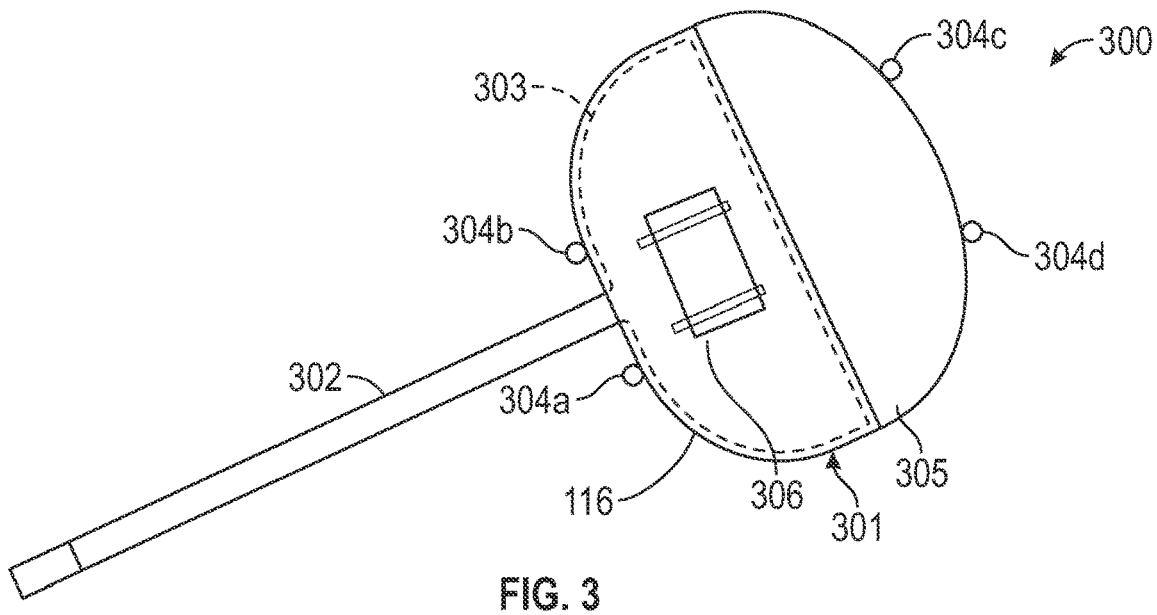
FIG. 3 is a top view showing an ocular electrolysis device.

The ocular electrolysis device 300 can be seen in FIG. 3. This ocular electrolysis device 300 can be used for treating glaucoma. FIG. 3 is a perspective view that illustrates one embodiment of the electrolysis device of the present inventions. An aqueous diverting tube 302 could extend from the device body 301 and may enter the electrolysis chamber 303. A plurality of eyelets 304a,b, c,d in the device body 301 could be provided to secure the ocular electrolysis device 300 to the surface of the eye 100. The device may have a top plate 305 and a roof 306 in the top plate 305. The ocular electrolysis device is constructed, for example, from a medical grade thermoplastic material including polypropylene, or a silicone material. A surface, such as the top plate or roof, of the ocular electrolysis device can be constructed from a gas-permeable material such as Tyvek, PMMA, Boston® II, Boston ES®, Boston® IV, Boston® Equalens®, Boston EOR, Boston® Equalens® II, Boston XOR, Boston XO2 ® and other contact lens materials, to allow the release of gas from the electrolysis chamber into the subconjunctival space or directly into the atmosphere.

The ocular electrolysis device 300 could be configured in the shape of an egg, with a wider end having the aqueous diverting tube 302. The top of the ocular electrolysis device 300 may have a dome shape to cover the electrolysis chamber 303 and the electronics. The bottom of the ocular electrolysis device 300 may have a semicircular upward spherical configuration to match the shape of the eyeball 100 so that the device can be mounted snugly on the surface of the sclera 103. The radius of curvature of the base of the ocular electrolysis device 300 is in the range of 10 to 14 mm to conform to the curvature of the sclera 103.

The diverting tube 302 is a hollow tube, (or shunt), perhaps a Pitot tube, about 24 to 26 mm in length and 0.75 to 1.25 mm in diameter. The diverting tube 302 may be inserted approximately 1 to 3 mm into the anterior chamber of an eye 100 allowing aqueous 112 to flow from the anterior chamber through the diverting tube 302 and into the electrolysis chamber 303 of the ocular electrolysis device 300.

The ocular electrolysis device 300 may have one or more eyelets 304a,b,c,d. The plurality of eyelets 304a,b,c,d are holes within the body or edge of the ocular electrolysis device 300 that may be used for suturing the ocular electrolysis device 300 to the eye 100. The plurality of eyelets 304a,b, c,d may be 1-2 mm in diameter and may extend through the height of the ocular electrolysis device 300.

In some embodiments, the ocular electrolysis device 300 has a device body 301 and a top plate 305. The device body 301 and top plate 305 may be attached together using any biocompatible method such as with a chemical method using a rubber adhesive, pitch, two-sided tape, water-based adhesives, solvent-based adhesives, reactive adhesives (polyurethane, acrylic, cyanoacrylate, polyimide, silicone, etc.), hot melt adhesives (hot glue, etc.), thermosetting adhesives (resin and hardener, etc.), pressure-sensitive adhesives, contact adhesives, epoxy adhesives, white glue (polyvinyl acetate), and similar. Alternatively, the base and top plate 305 could be mechanically attached with a clip mechanism, a nail, a staple, a screw, a nut and bolt, a pin, a cotter pin, rivets, clevis pins, dowel pins, integral fasteners, friction, heat fused, snapped together, or attached with other similar methods.

Inside the ocular electrolysis device 300, between the device body 301 and the top plate 305, is an electrolysis chamber 303. The diverting tube 302 is attached to one end of the electrolysis chamber 303 and allows aqueous 112 to fill the electrolysis chamber 303. The intraocular pressure in the eye 100 also creates a pressure in the electrolysis chamber 303. A pressure sensor 504 may be located in the electrolysis chamber 303 as well as the electrodes 401.

The placement of electrodes 401 external to the surface of the eye and within the electrolysis chamber is preferable to electrodes placed inside the eye because external electrodes 401 will not generate heat inside the eye with thermal side effects. Electrodes within the eye 100 can generate toxic by-products inside the eye 100 such as chlorine gas and metallic fragments from the electrodes. Electrodes 401 situated on the outside of the eye 100 are less likely to cause toxic by-products or metallic fragments inside the eye 100, or intraocular chlorine gas that can be harmful. Electrodes 401 situated outside of the eye 100 are easier to repair or replace. Unlike internal electrodes, external electrodes 401 do not touch vital anatomic structures inside the eye 100 except for aqueous humor 112. Therefore, the risk of damage to internal eye structures is less. Unlike external electrodes, internal electrodes require an extensive invasive procedure for repair or replacement. External electrodes 401 are not invasive and do not penetrate the eye 100 since they are contained within the body of the ocular electrolysis device 300. External electrodes 401 do not require an incision into the eye. Internal electrodes require a large incision, even when enclosed in a tube shunt, and are therefore more likely to lead to infection and other complications. External electrodes within the ocular electrolysis chamber are therefore safer than electrodes that are inserted into the eye.

Figure 4:
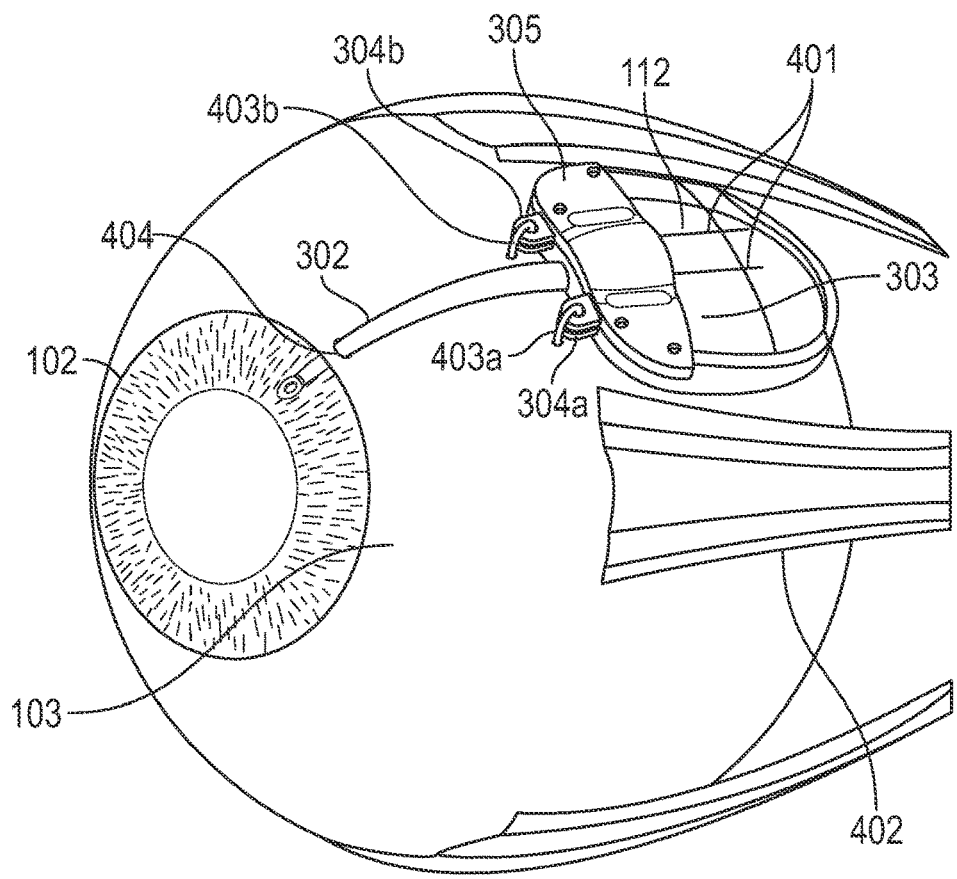
FIG. 4 is a perspective view of an ocular electrolysis device installed on a mammalian eye showing the fluid flow.

FIG. 4 is a perspective view that illustrates the ocular electrolysis device 300 with partial removal of the top plate 305. The distal opening of the diverting tube 302 in the anterior chamber 102 draws aqueous 112 into the electrolysis chamber 303. Electrodes 401 in the electrolysis chamber 303 provide electric current for electrolysis. The ocular electrolysis device 300 is fastened to the sclera 103 with suture 403a,b or conventional tissue glue. The device is located between extraocular muscles 402 of the eye 100.

In FIG. 4, an incision 404 could be made in the sclera 103 of the eye 100 posterior to the cornea 101. The diverting tube 302 is inserted in the incision 404 extending above the iris 107 and behind the cornea 101 and into the aqueous 112 in the anterior chamber 102. Aqueous that passes from the anterior chamber through the distal opening of the diverting tube 302 fills the electrolysis chamber 303. The electrolysis chamber has two electrodes 401 that when activated with electrical current provided by a power source, converts the aqueous 112 into oxygen and hydrogen gas. The gasses pass through a gas-permeable material in a surface, such as the roof or top plate, of the ocular electrolysis device.

In the FIG. 4 embodiment, the plurality of eyelets 304a,b are attached to the edge of the device body 301 of the ocular electrolysis device 300. In other embodiments, the plurality of eyelets 304a,b,c,d could be placed within the device body 301. The plurality of eyelets 304a,b are sutured to the sclera 103 of the eye 100 with a suture 403a,b. In other embodiments, the ocular electrolysis device 300 could be adhered to the sclera 103 of the eye 100 with a tissue adhesive.

Figure 5:
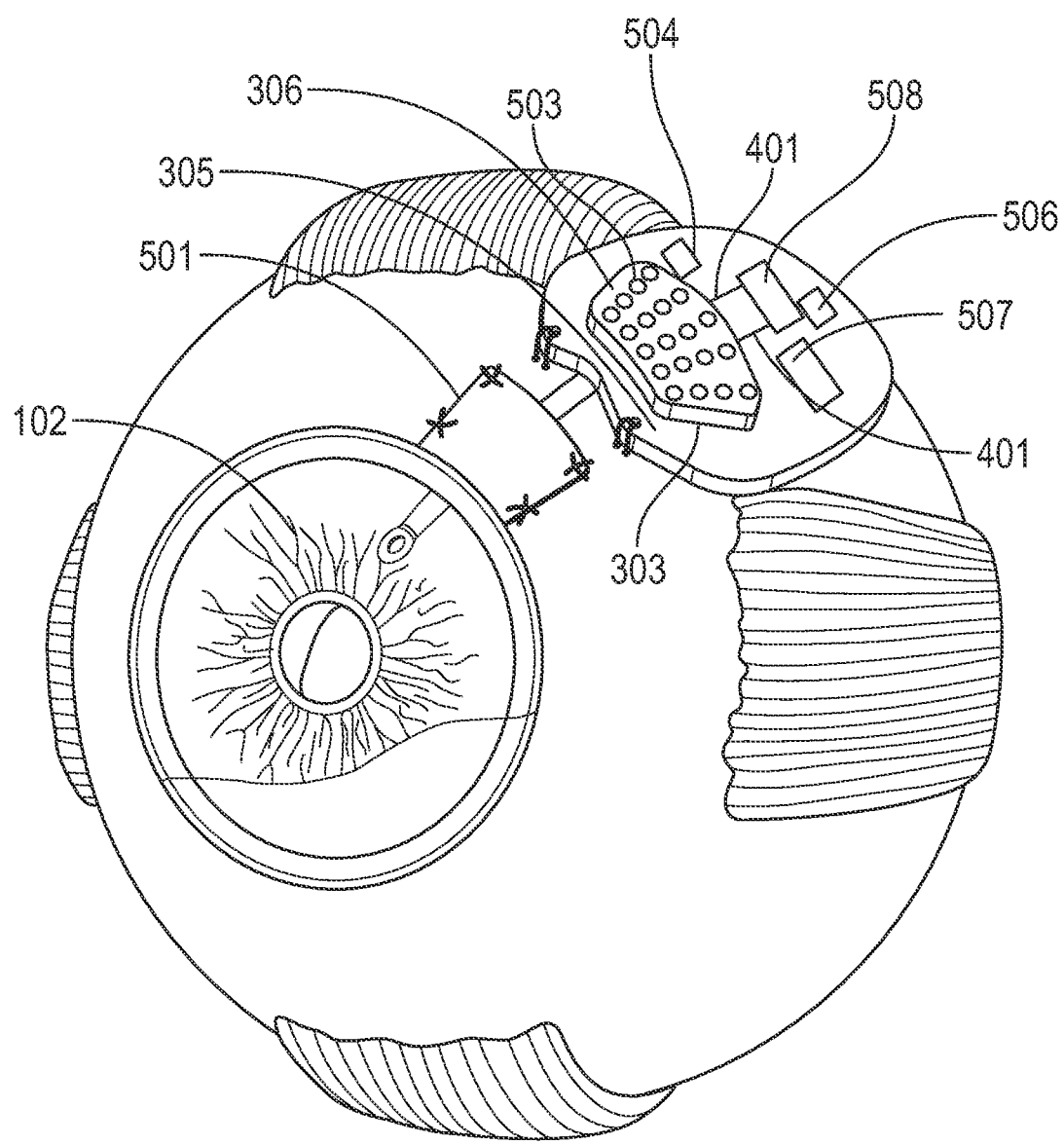
FIG. 5 is a perspective view of an ocular electrolysis device installed on a mammalian eye showing the device components.

FIG. 5 is a perspective view that illustrates an embodiment of the ocular electrolysis device 300 wherein the diverting tube 302 is tunneled under a scleral flap 501 prior to entering the anterior chamber 102. The electrolysis chamber 303 has a roof 306 in the top plate 305 that has perforations 503 or a gas-permeable material that permits the release of gas produced by electrolysis. The internal body of the electrolysis device 300 has a pressure sensor 504, a power source 506, a controller 507, and a regulator 508 that regulates voltage and current delivered to the electrodes 401 in the electrolysis chamber 303. The controller 507 is configured to provide transmission of data to an outside receiver such as a cellular phone or desktop computer, and to receive wireless communication.

FIGS. 3 through 5 illustrate one embodiment of the present electrolysis device 300 constructed in accordance with the present inventions positioned on the scleral surface 103 of an eye 100. The present inventions are designed for the treatment of glaucoma by diverting aqueous 112 in the anterior chamber 102 of an eye 100 into an electrolysis chamber 303 of the ocular electrolysis device 300. The ocular electrolysis device 300 comprises a pliable device body 301 that is positioned on the scleral surface 103. A top plate 305 is oppositely disposed to the device body 301 and contains a roof 306 for the ocular electrolysis device 300. The coincident edges of the ocular electrolysis device 300 could have a beveled taper to facilitate placement on the surface of the eye 100. The thickness of the plates 310,305 could be in the range of 0.25 to 2.5 mm.

The size of the roof 306 may approximate the top of the electrolysis chamber 303 and could consist of a material that is permeable to gas but impervious to fluids. Suitable materials from which to make the roof may include Tyvek, Temish, Teflon, Gore-Tex, and materials used in contact lenses. In another embodiment, the roof 306 consists of a grated cover that is perforated with holes about 0.25 to 0.5 mm in diameter to permit the escape of gases. The surface tension of aqueous humor 112 could prevent it from escaping through a grating with small perforations.

The device body 301 and top plate 305 may accommodate a diverting tube 302 that extends from the electrolysis chamber 303 across the surface of the eye 100 and into the anterior chamber 102. The ocular electrolysis device 300, including diverting tube 302, may be composed of an elastomeric polymer such as silicone. Other suitable materials for the ocular electrolysis device 300 include siliconized rubber, polypropylene, and polymethylmethacrylate. A radiopaque material such as Barium Sulfate may be added to the polymer so that it can be visible in a radiologic study.

The ocular electrolysis device 300 and the diverting tube 302 are implanted on the scleral surface 103. The diverting tube 302 is placed through an incision 404 created in the conjunctiva 105 and into the space between the sclera 103 and conjunctiva 105. Alternatively, the device can be placed between the scleral surface 103 and Tenon's capsule 104. The exposed portion of the diverting tube 302 and or the ocular electrolysis device 300 can be covered with graft material consisting of sclera, amniotic tissue, or pericardium. The ocular electrolysis device 300 is generally curved and has a footprint on the surface of the eye 100 could be in the range of 50 to 500 mm². The radius of curvature of the base of the device is in the range of 10 to 14 mm to conform to the curvature of the sclera 13. The length of the plates could be no more than 13 mm and could be about 10 mm.

The diverting tube 302 could be a Pitot tube, approximately 24 to 26 mm in length. The ocular electrolysis device 300 and diverting tube 302 can be secured to the scleral surface 103 with a suture 403a,b through eyelets 304a,b situated at the outer border of the ocular electrolysis device 300, or by a conventional tissue adhesive.

The distal end of the diverting tube 302 extends from the ocular electrolysis device 300 through the cornea 101 and into the anterior chamber 102. The diverting tube 302 is secured to the ocular electrolysis device 300 by any biocompatible method such as with a chemical adhesion method with a rubber adhesive, pitch, two-sided tape, water-based adhesives, solvent-based adhesives, reactive adhesives (polyurethane, acrylic, cyanoacrylate, polyimide, silicone, etc.), hot melt adhesives (hot glue, etc.), tissue glue, thermosetting adhesives (resin and hardener, etc.), pressure-sensitive adhesives, contact adhesives, epoxy adhesives, white glue (polyvinyl acetate), and similar. Alternatively, the diverting tube 302 and the ocular electrolysis device 300 could be mechanically attached with a clip mechanism, a nail, a staple, a screw, a nut and bolt, a pin, a cotter pin, rivets, clevis pins, dowel pins, integral fasteners, friction, heat fused, snapped together, or attached with other similar methods. The proximal end of the diverting tube 302 enters the opening of the electrolysis chamber 303. Aqueous 112 flows through the diverting tube 302 and into the electrolysis chamber 303.

The electrolysis chamber 303 could have a pressure sensor 504 that measures the pressure of aqueous fluid 112 within the electrolysis chamber 303. A pair of electrodes 401 could extend from the controller 507 into the electrolysis chamber 303. Aqueous 112 contained within the electrolysis chamber 303 is the target tissue for receiving electrical stimulation. Pressure measurements by the pressure sensor 504 may be conveyed to a controller 507 that could regulate the duration and amount of current that is provided to electrodes 401 within the electrolysis chamber 303. The controller 507 could generate pulses to a pair of electrodes that conduct current and project into the electrolysis chamber 303. The controller 507 could accept adjustments to its program remotely to adjust for a desired pressure threshold.

The electrodes 401 could have a length between about 100 microns to about 750 microns and a width of about 0.5 mm to about 1.5 mm. The electrodes 401 may be composed of one or a plurality of materials including titanium, nickel-titanium, titanium nitride, graphite, nickel, aluminum, platinum, brass, aluminum, iridium oxide, tantalum, stainless steel, alloys, or a combination thereof. The electrodes 401 may include tines.

In one embodiment, the electrodes 401 are manufactured with a medical-grade metallic substance that is safe for prolonged use. The efficiency of electrolysis is affected by current density, temperature, inclination angle, spacing between electrodes, and their surface wettability. A portion of the electrodes 401 that does not extend into the electrolysis chamber 303 may be embedded in a non-conductive sheath that serves as an insulating barrier.

The electrical current delivered to electrodes 401 may include a current having a pulse amplitude between about 250 microamps to 25 milliamps. The current may include a pulse amplitude, a pulse width, and a pulse frequency, and one or more of the pulse amplitude, pulse width, or pulse frequency which may be varied over the treatment period. The current may have a pulse frequency between about 2 Hz to about 270 Hz. The current may include a current having a pulse width between about 50 microseconds to about 2700 microseconds. The magnetic field generated by current to the electrodes 401 may have a frequency of about 10 kHz to about 1000 MHz.

A power source 506 such as a rechargeable battery, including lithium-ion or lithium polymer, a photovoltaic cell, a biofuel cell, piezoelectric material, magnetic induction, or a capacitor, contained within the internal body of the ocular electrolysis device 300, provides power to the pressure sensor 504, controller 507, regulator 508, and electrodes 401. When the magnetic field has varying amplitude, the tuning capacitor stores charge. A diode may be implemented to rectify a current signal. The voltage may be between 10 microvolts and 25 microvolts and an alternating current with a frequency of 2 Hz to 1000 Hz.

A power source 506 can be recharged by a radio-frequency identification, or "RFID," link or other type of electric recharging circuit. Alternatively, power can be received wirelessly through magnetic inductance and refined with a QI Wireless Charger chip such as an Analog Devices LTC4124 to transform the power to allow for battery charging. In another embodiment, a miniature solar cell on the top plate 305 could be used to recharge the power source 506. In still another embodiment, a thermoelectric generation heat exchange device is used to use the heat from a blood vessel to generate the power for the ocular electrolysis device 300. The thermoelectric generator can be used to recharge the power source 506.

Gases produced by electrolysis are released through the roof 306 of the electrolysis chamber 303. The composition of the roof 306 permits gasses to escape but retains fluids that remain in the electrolysis chamber 303.

In another embodiment, the subject inventions have a controller module 507 for data transmission through an antenna 701 that provides wireless transmission of information provided by the pressure sensor 504. Data transmission by the module can include date and time-stamped measurements of intraocular pressure, an alert message for low battery voltage measurements, and intraocular pressure measurements that are above or below selected thresholds as well as other status information. The controller module 507 can also receive communication to adjust thresholds for the delivery of electrical current to electrodes within the electrolysis chamber.

The subject inventions can be implanted by conventional surgery techniques that are well-known in the field of ophthalmology. The surgical implant procedure is initiated with a slit incision 404 in the conjunctiva 105 and Tenon's capsule 104 in a quadrant of the eye 100 intended for implantation. The ocular electrolysis device 300 may be placed between a pair of rectus muscles 402. The ocular electrolysis device 300 and trailing diverting tube 302 may be inserted through this incision 404 and placed between the conjunctiva 105 or Tenon's capsule 104 and sclera 103. Alternatively, the diverting tube 302 can be placed in a scleral tunnel canal 121 that leads to the anterior chamber 102. The diverting tube 302 extending from the ocular electrolysis device 300 is inserted through a limbal incision approximately 1.5 mm in diameter. The eyelets 304*a,b* situated in the ocular electrolysis device 300 are threaded with sutures 403*a,b* to secure the ocular electrolysis device 300 on the sclera 103. Alternatively, a medically approved adhesive such as cyanoacrylate, polyethylene glycol hydrogel, fibrin sealant, or tissue glue with adequate adhesive properties can be used to secure the ocular electrolysis device 300 on the sclera 103.

Figure 6:
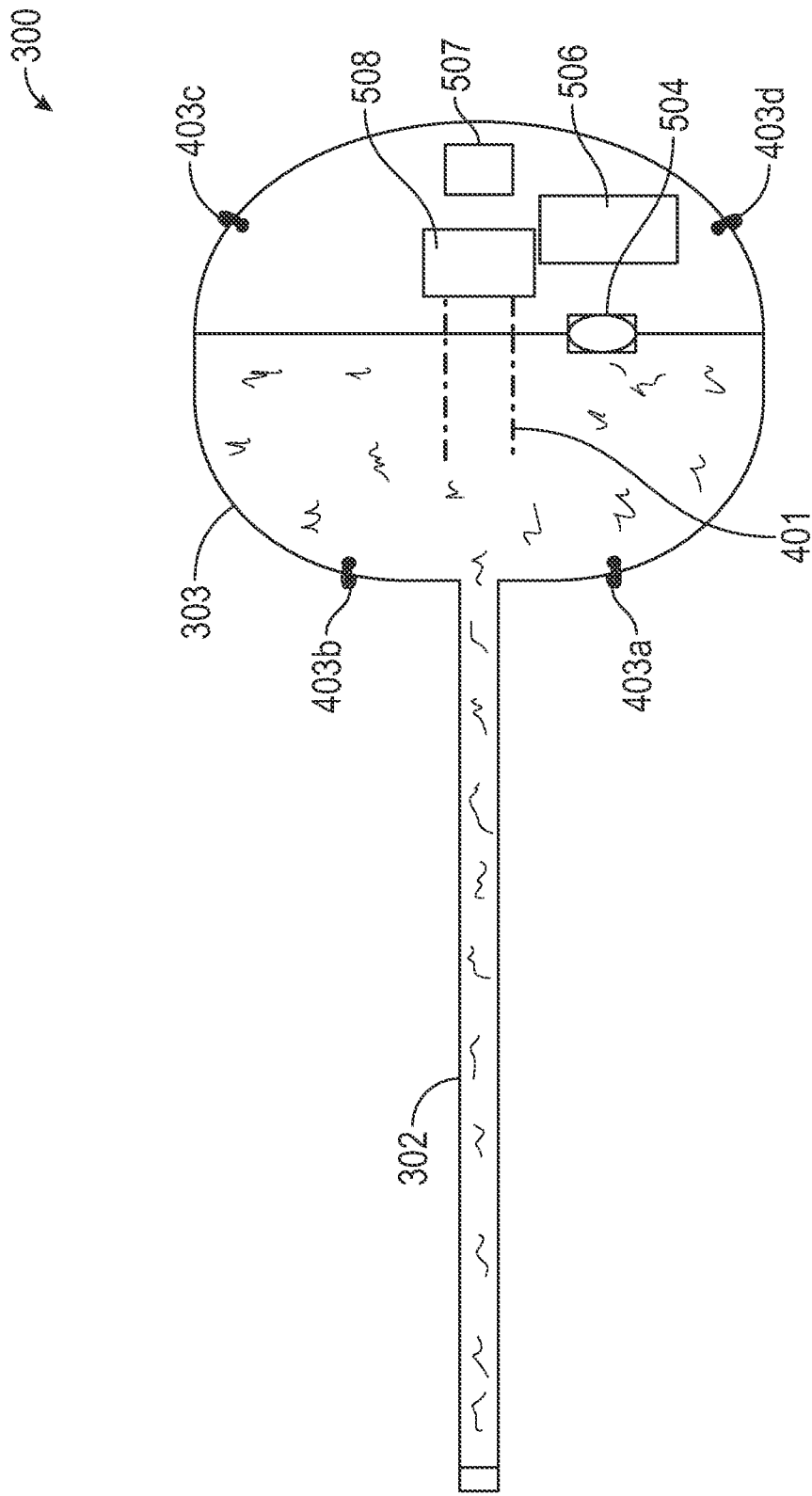
FIG. 6 is a cross-section of an ocular electrolysis device.

FIG. 6 shows a cross-section of the ocular electrolysis device 300. The diverting tube 302 delivers aqueous 112 from the anterior chamber 102 to the electrolysis chamber 303 of the ocular electrolysis device 300. The electrolysis chamber 303 comprises a portion of the area of the ocular electrolysis device 300. The other portion, in this embodiment, comprises the electronics. The electrodes 401 pass from the electronics area into the electrolysis chamber 303. The pressure sensor 504 also transcends the barrier between the electrolysis chamber 303 and the electronics. In some embodiments, the electrolysis chamber 303 could be above a printed circuit board holding the electronics. In some embodiments, the electronics could be covered with a fluid impervious material such as an epoxy, with the electrodes 401 and the pressure sensor 504 extending through a fluid impervious material.

The ocular electrolysis device 300 in this embodiment has four eyelets 403*a,b,c,d* attached to the device body 301.

The electronics include a controller 507 for operating the ocular electrolysis device 300. In one embodiment, the controller 507 is a Cypress C4BT-423028-02 Bluetooth Low Energy (BLE) system on a chip. The controller 507 could be mounted on a printed circuit board. In some embodiments, the printed circuit board is flexible. The controller 507 could be electrically connected to the pressure sensor 504, receiving signals indicating the pressure detected in the electrolysis chamber 303 from the pressure sensor 504. The controller 507 may also pass signals to the pressure sensor 504 indicating parameters for determining, filtering, and adjusting the pressure readings. In some embodiments, there is a regulator 508 between the controller 507 and the electrodes 401. The regulator may pass power (voltage and current) from the controller 507 to the electrodes 401, adjusting the signal from the controller 507 to direct the voltage, current, frequency, and duration of the power that controls the electrolysis in the electrolysis chamber 303 by controlling the electrical characteristics of the power at the electrodes 401. The controller 507 could be electrically connected and receive power from power source 506.

Figure 7:
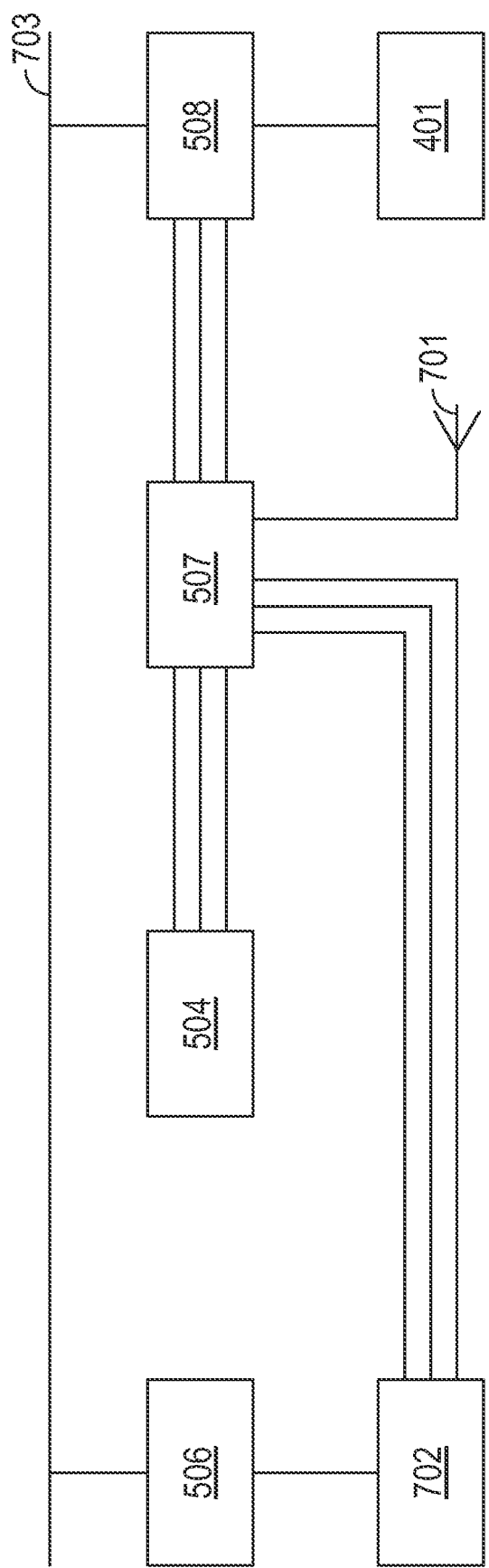
FIG. 7 is a block diagram of the electrical components of an ocular electrolysis device.

FIG. 7 is an electrical diagram of one embodiment of the ocular electrolysis device 300. The controller 507 could be a BLE System on a Chip such as a Cypress C4BT-423028-02. The Cypress BLE Chip includes an ARM microprocessor, and Bluetooth low energy module (which includes a transceiver) for communications via the Bluetooth protocol with a cell phone, computer, or other Bluetooth devices, 1024 KB Flash RAM, 512 KB SRAM, and numerous input and output pins for interfacing with other devices, such as antenna 701, power source 506, pressure sensor 504, regulator 508, and wireless recharging circuitry 702. The controller 507 may contain features that allow the controller 507 to go into a sleep mode until woken by a timer or with the reception of a Bluetooth message. This may allow the ocular electrolysis device 300 to go to sleep for periods of time, perhaps minutes, hours, or days, and then wake up to check the pressure in the eye 100. In some embodiments, this period for sleeping is configurable through the Bluetooth connection. The ocular electrolysis device 300 could also be woken up through Bluetooth communication.

In the FIG. 7 embodiment, the controller 507 is electrically connected to the power source 506 through a power rail 703, receiving power from the power source 506 and perhaps sensing the remaining power in the power source 506. The controller 507 may also control wireless recharging by sending signals and receiving signals from the wireless recharging circuitry 702.

The controller 507 may be connected to antenna 701 for sending signals to a computer or to a smartphone. In some embodiments, the communications is using the Bluetooth protocol. Other embodiments may use WiFi (IEEE 802.11). Still other embodiments may use cellular communications (commonly known as 3G, 4G, and/or 5G). Other standard or proprietary protocols could also be used.

The controller 507 could be electrically connected to the pressure sensor 504. In one embodiment, the controller 507 passes power to the pressure sensor 504. In other embodiments, the pressure sensor 504 is electrically connected to and receives power directly from power source 506. In some embodiments, the pressure sensor 504 both sends and receives signals from the controller 507. The signals may include current pressure readings and pressure sensor 504 configuration settings. In some embodiments, the pressure sensor is connected to the power rail 703 and in other embodiments it derives its power through the controller 507.

The controller 507 also controls, and is electrically connected to, the electrodes 401. In some embodiments, the controller 507 will directly power the electrodes 401. Some controllers 507 have analog ports with sufficient power to create electrolysis straight from the chip. In other embodiments, a regulator 508 is used to regulate the power to the electrodes 401. In this case, the controller 507 is electrically connected to the electrodes 401 through the regulator 508. The regulator 508 in this embodiment electrically connects to the power source 506 (and/or the power rail 703) to receive power and is electrically connected to the controller 507 to receive signals indicating the power characteristics to be sent to the electrodes 401. These characteristics may include voltage, current, frequency, and duration.

FIG. 8 is a functional flow chart of one possible embodiment of the operation of the ocular electrolysis device 300 and the treatment of glaucoma with the ocular electrolysis device 300. The details of the software operation will be seen in FIG. 9.

The operation of the ocular electrolysis device 300 begins with the implantation of the ocular electrolysis device 300 onto the surface of the eye 100. An incision 404 is made in the eye 100 and the diverting tube 302 is inserted into the anterior chamber 102 of the eye. See step 801.

Next, in step 802, the pressure in the eye 100 is transmitted by the aqueous 112 in the anterior chamber 102 down the diverting tube 302 into the electrolysis chamber 303 of the ocular electrolysis device 300. A pressure sensor 504 located in the electrolysis chamber 303 measures the pressure, determining the pressure in the eye 100.

In step 803, the pressure sensor 504 sends signals indicating the pressure to the controller 507. The controller 507 reads the pressure signals and converts the signals into a number for processing. The controller 507 determines if the pressure in the eye 100 is high or low. If the pressure is high, the controller determines the optimal voltage, current, frequency, and duration to deliver to the electrodes 401 in order to reduce the pressure in the eye 100 by creating an electrolysis reaction in the aqueous 112 in the electrolysis chamber 303. As the electrolysis reaction in the aqueous 112 happens, the pressure sensor 504 monitors the pressure in the electrolysis chamber 303, reporting the pressure to the controller 507 so that the controller can modify or stop the electrolysis reaction in the aqueous 112 by controlling the voltage, current, frequency, and duration to deliver to the electrodes 401.

In step 804, the electrolysis in the electrolysis chamber 303 results in the production of gas, primarily $O_2$ and $H_2$. The gas escapes from the gas-permeable surface, such as the roof 306. The power source 506 and the controller 507 continue to monitor the pressure until the pressure reaches a programmed threshold. The controller 507 also watches for an increase in pressure, possibly indicating that the roof 306 is unable to release the gas. In this case, the controller 507 may shut down the operation and notify a user through the communications link and the antenna 701.

The controller 507 may be programmed, in step 805, to communicate with the user through the antenna 701 to warn the user of power issues, over-pressure, and under-pressure situations. The controller 507 also may transmit the current pressure reading or a data structure with historical pressure readings. For instance, an array containing the pressure readings along with a date and time stamp and information on the voltage, current, and frequency of the power on the electrodes 401 may be transmitted. The controller 507 may also receive settings and configuration information from the user via the antenna 701. These settings may include pressure thresholds to turn the electrodes 401 on and off, thresholds for critical high-pressure and critical low-pressure, sleep time between pressure readings, and voltage, current, and frequency of the power on the electrodes 401 for one or more pressure levels.

Figure 9:
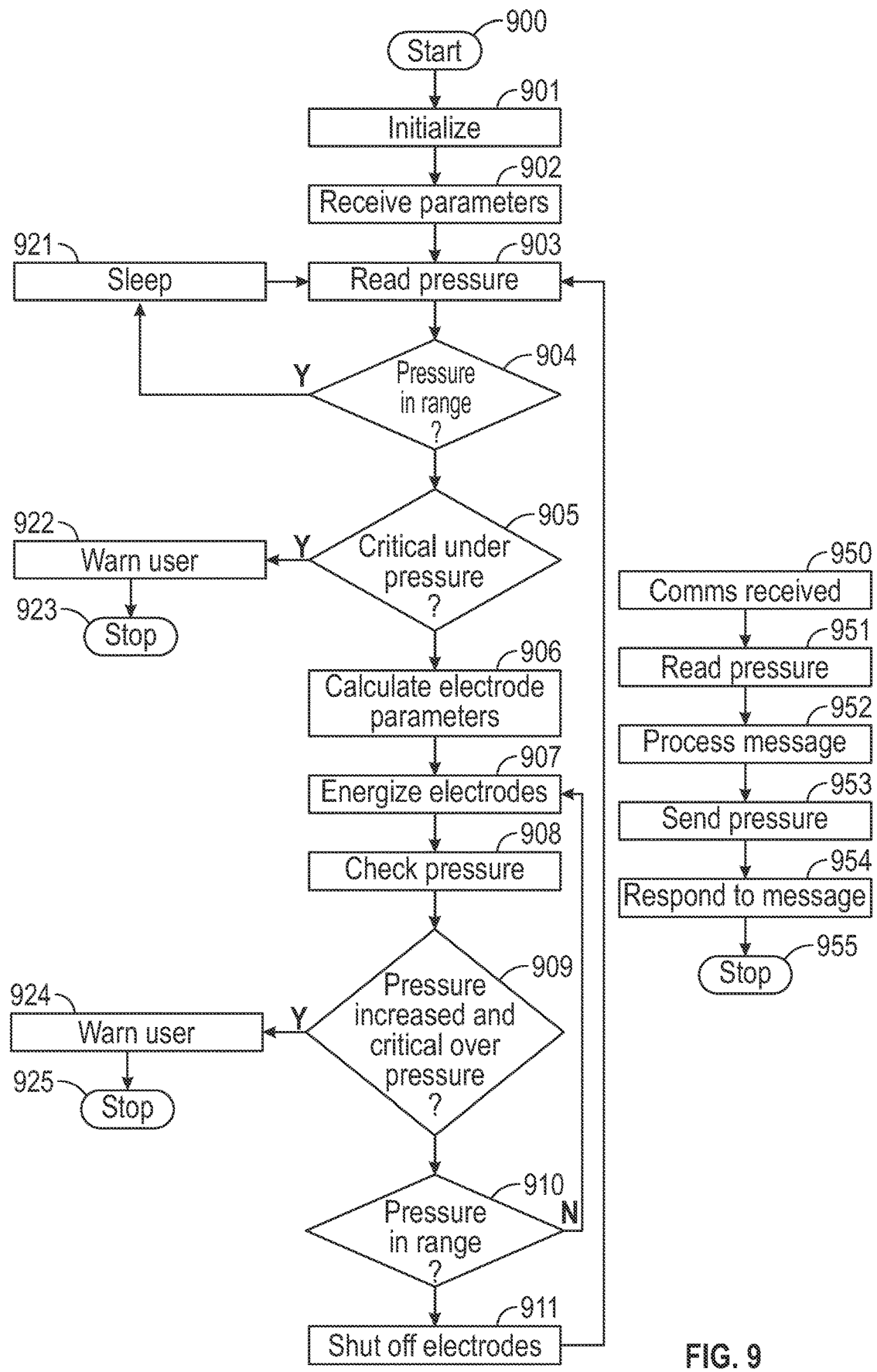
FIG. 9 is a block diagram of the software components of an ocular electrolysis device.

FIG. 9 is a flowchart of one possible software implementation of the ocular electrolysis device 300. This flowchart could be implemented as non-transient machine-readable instructions stored in the memory of the controller 507 that instruct the controller 507 to perform the flowchart. This figure shows two parallel processes, one handling the operation of the ocular electrolysis device 300 and the other processing the communications for the ocular electrolysis device 300. When a communications message arrives 950, the ocular electrolysis device 300 is interrupted and the message is processed. Because eye 100 pressure is so critical to the ocular electrolysis device 300, in one embodiment the pressure is read from the pressure sensor 504 for each message that arrives 951. The message is then processed 952, for instance, a parameter may be changed or pressure data collected. Then the pressure value 953 and the message response 954 are sent to the antenna 701. The thread then stops 955. In some embodiments, all steps 950-955 are processed in an interrupt handler. In other embodiments, steps 950-955 are handled in a separate thread with interrupts still enabled. The order of steps 951-955 can be changed in other embodiments, for instance, the message can be processed 952 before reading the pressure 951. In other embodiments, the reading of the pressure 951 and the sending of the pressure reading could be eliminated or only occur if the message specifically asks for a pressure reading.

Messages received at the ocular electrolysis device 300 may include messages to reset the ocular electrolysis device 300 or messages to shut off the ocular electrolysis device 300, perhaps in an emergency situation. Both a reset or a shut-off message would turn the electrodes 401 off.

The main thread of the ocular electrolysis device 300 software operation starts 900 by initializing 901 the ocular electrolysis device 300. Parameters are set to default 902 or uploaded over the communications interface. The pressure sensor 504 is set up and turned on. The regulator 508 is also set up and the current to the electrodes 401 is turned off. The communications transceivers in the controller 507 are initialized. Power is checked and the wireless recharging circuitry 702 is initialized.

Then the pressure is read 903 from the pressure sensor 504 and stored in memory. If the pressure is in range 904, then the ocular electrolysis device 300 is put to sleep 921 for a configurable period of time. The sleep time could be seconds, minutes, hours, or days, depending on how the device is configured. In some embodiments, the user could set this parameter through the communications channel. In some embodiments, the sleep time could vary based upon the pressure value so that if the pressure is close to a threshold, then the ocular electrolysis device 300 sleeps for a shorter period than if the eye 100 pressure is low. When the ocular electrolysis device 300 wakes up from sleeping, it reads the pressure 903 again.

If the pressure is not in range 904, then the pressure is checked to see if the pressure is critically under pressure 905. If the pressure is below the critical low threshold, then a message is sent to the user 922 warning of the situation, and the ocular electrolysis device 300 stops 923. Critically low pressure could be caused by a leak of the aqueous 112 in the ocular electrolysis device 300, so the device is stopped until a user or a physician addresses the situation. In some embodiments, a valve could be installed on the diverting tube 302, and this valve could be electrically closed to prevent leakage of the aqueous 112.

If the pressure is not critically under pressure 905, then the electrodes 401 parameters for the regulator 508 are calculated 906 and the electrodes 401 are energized 907. This will cause the electrolysis reaction to occur in the electrolysis chamber 303, converting the aqueous 112 into a gas.

Next, the pressure is checked 908 by the pressure sensor 504. If the eye 100 pressure has increased from the previous reading and the pressure is critically over pressure 909, then the user is warned 924 of the situation, the current to the electrodes 401 is reduced or turned off, and the ocular electrolysis device 300 is modified 925. One possible cause is that the roof 306 is blocked and no longer allowing gas to escape. This may require action from the user or from a physician.

If the eye 100 pressure has not increased from the previous reading and/or the pressure is not critically over pressure 909, then the pressure is checked to see if the pressure is in range 910 to continue electrolysis. This range may be different from the range in 904 so as to prevent the ocular electrolysis device 300 from turning on and off with short cycles. It may be desirable to have the device turn on at a higher threshold and off at a lower value. If the pressure is not in range 910, then the electrodes 401 continue to be energized 907. If the pressure is in range 910, then the current to the electrodes 401 is reduced or turned off 911, and the ocular electrolysis device 300 is modified 925.

In other embodiments, the software could periodically check for issues with the power source 506 such as a low battery situation. The software could also check for a malfunction in the pressure sensor 504, the regulator 508, or the controller 507. In each situation, the software could send a message to a user regarding the issue.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies.

The foregoing devices and operations, including their implementation, will be familiar to, and understood by, those having ordinary skill in the art. This specification contains numerous dimensions, all of which could be changed without deviating from the inventions herein.

The above description of the embodiments, alternative embodiments, and specific examples, are given by way of illustration and should not be viewed as limiting. Further, many changes and modifications within the scope of the present embodiments may be made without departing from the spirit thereof, and the present inventions include such changes and modifications.

The invention claimed is:

1. An ocular electrolysis device comprising:
a diverting tube configured for insertion into an eye;
an electrolysis chamber mechanically attached to the diverting tube such that aqueous from the eye enters the electrolysis chamber through the diverting tube, where the electrolysis chamber has a gas-permeable surface that is impervious to non-gaseous aqueous;
a pressure sensor located in the electrolysis chamber;
a pair of electrodes located in the electrolysis chamber;
a power source electrically connected to a controller; and
the controller electrically connected to the pair of the electrodes and the pressure sensor, where the controller regulates electrolysis in the electrolysis chamber based on input from the pressure sensor through power levels at the pair of the electrodes.

2. The ocular electrolysis device of claim 1 configured for attachment to the eye.

3. The ocular electrolysis device of claim 2 further comprising eyelets for facilitating the attachment to the eye.

4. The ocular electrolysis device of claim 1 where the electrolysis chamber has a surface with perforations.

5. The ocular electrolysis device of claim 1 further comprising a voltage regulator electrically connected to the pair of the electrodes and the controller.

6. The ocular electrolysis device of claim 1 further comprising an antenna electrically connected to the controller.

7. The ocular electrolysis device of claim 1 wherein the power source includes a solar cell.

8. A method for treating glaucoma comprising:
implanting an ocular electrolysis device on a surface of an eye;
inserting a diverting tube attached to the ocular electrolysis device into an anterior chamber of the eye, where aqueous from the anterior chamber flows into a electrolysis chamber in the ocular electrolysis device;
measuring a pressure measurement in the eye with a pressure sensor located in the electrolysis chamber;
reading the pressure measurement with a controller, said controller electrically connected to the pressure sensor;
applying current and voltage from a power source under direction of the controller to a pair of electrodes in the electrolysis chamber, causing electrolysis of the aqueous to occur in the electrolysis chamber;
allowing gas produced by the electrolysis to escape through a gas permeable surface of the electrolysis chamber, where the gas permeable surface is impervious to non-gaseous aqueous; and
directing, by the controller, the current and the voltage based on the pressure measurement.

9. The method for treating the glaucoma of claim 8 further comprising using the pressure measurement read by the controller to determine the voltage to apply to the pair of the electrodes.

10. The method for treating the glaucoma of claim 8 further comprising using the pressure measurement read by the controller to determine the current to apply to the pair of the electrodes.

11. The method for treating the glaucoma of claim 8 further comprising using the pressure measurement read by the controller to determine a frequency of the voltage to apply to the pair of the electrodes.

12. The method for treating the glaucoma of claim 8 further comprising sending, via an antenna, a message with information regarding the ocular electrolysis device.

13. The method for treating the glaucoma of claim 12 where the information is the pressure measurement of the aqueous.

14. The method for treating the glaucoma of claim 12 where the information relates to a status of the power source.

15. The method for treating the glaucoma of claim 8 further comprising receiving, via an antenna, a message with a parameter for the ocular electrolysis device.

16. The method for treating the glaucoma of claim 15 where the parameter includes a threshold for the pressure measurement of the aqueous.

17. The method for treating the glaucoma of claim 15 where the parameter is a critical low-pressure threshold for the pressure measurement of the aqueous.

18. The method for treating the glaucoma of claim 17 further comprising turning off the current to the electrodes by the controller when the pressure measurement of the aqueous is below the critical low-pressure threshold.

19. The method for treating the glaucoma of claim 15 where the parameter is a critical high-pressure threshold for the pressure measurement of the aqueous.

20. The method for treating the glaucoma of claim 19 further comprising turning off the current to the electrodes by the controller when the pressure measurement of the aqueous is above the critical high-pressure threshold and when the pressure measurement of the aqueous is increasing.

* * * * *